US00PP36304P2

(12) United States Plant Patent
Farrow

(10) Patent No.: US PP36,304 P2
(45) Date of Patent: Dec. 10, 2024

(54) ***CAMELLIA* PLANT NAMED 'FARROWCJWD'**

(50) Latin Name: ***Camellia* hybrid**
Varietal Denomination: FARROWCJWD

(71) Applicant: Spring Meadow Nursery, Inc., Grand Haven, MI (US)

(72) Inventor: Michael W. Farrow, Warwick, MD (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 5 days.

(21) Appl. No.: 18/541,312

(22) Filed: Dec. 15, 2023

(51) Int. Cl.
*A01H 5/02* (2018.01)
*A01H 6/00* (2018.01)

(52) U.S. Cl.
USPC ..... Plt./243
CPC ..... *A01H 6/00* (2018.05)

(58) Field of Classification Search
USPC ..... Plt./243
CPC ..... A01H 5/02
See application file for complete search history.

*Primary Examiner* — Kent L Bell
(74) *Attorney, Agent, or Firm* — Cassandra Bright

(57) ABSTRACT

A new and distinct cultivar of *Camellia* plant named 'FARROWCJWD' is disclosed, characterized by abundant production of fully double, pure white flowers, and glossy, dark green foliage. Plants are well-branched, with good container performance and cold hardy to at least USDA zone 7 and possibly 6b. The new cultivar is a *Camellia*, suitable for ornamental garden purposes.

3 Drawing Sheets

Latin name of the genus and species: *Camellia* hybrid.
Cultivar denomination: 'FARROWCJWD'.

BACKGROUND OF THE INVENTION

The new cultivar is a product of a planned breeding program by the inventor. The open-pollination resulting in the new cultivar was made during 2009, at a nursery in Earleville, Maryland. The seed parent is the unpatented cultivar *Camellia* 'Winter's Joy'. The pollen parent is unidentified. The inventor discovered this new cultivar at the same nursery in 2013.

After identifying the new cultivar as a potentially interesting selection, the inventor first propagated plants of 'FARROWCJWD' by hardwood vegetative cuttings during 2013 at the same nursery in Earleville, Maryland. Multiple generations have been reproduced and have shown that the unique features of this cultivar are stable and reproduced true to type.

Date of the first public disclosure was Jun. 27, 2023, occurring in Grand Haven, Michigan. This disclosure was made directly by the inventor or one who obtained the claimed invention directly or indirectly from the inventor. This disclosure and all public disclosures made between Jun. 27, 2023 and the filing of this application fall within the exception allowed under 102(b)(1).

SUMMARY OF THE INVENTION

The cultivar 'FARROWCJWD' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'FARROWCJWD'. These characteristics in combination distinguish 'FARROWCJWD' as a new and distinct *Camellia* cultivar:

1. Fully double, pure white flowers.
2. Abundant flowers.
3. Hardiness USDA 7(6b)-9.
4. Attractive, healthy, glossy, dark green foliage.
5. Upright, well-branched habit which lends itself to good container performance.

COMPARISON TO PARENT CULTIVAR

'FARROWCJWD' is similar in most horticultural characteristics to the seed parent cultivar *Camellia* 'Winter's Joy'. Plants of the new cultivar 'FARROWCJWD' are similar to plants of the seed parent in most horticultural characteristics, however, differ in the following:

1. Plants of the new cultivar have a tight, upright habit, while plants of the seed parent have a teardrop-shaped habit.
2. Flowering period of the new cultivar is longer than the flowering period of the seed parent.
3. Foliage color of the new cultivar is darker green than foliage color of the seed parent.

COMMERCIAL COMPARISON

'FARROWCJWD' can be compared to the commercial cultivar *Camellia* 'Winter's Snowman', unpatented. Plants of the new cultivar 'FARROWCJWD' are similar to plants of 'Winter's Snowman' in most horticultural characteristics, however, plants of the new cultivar 'FARROWCJWD' differ in the following:

1. Plants of the new cultivar have a tighter, well-branched habit, while plants of this comparator have a looser, rangier habit.

2. Flowers and buds of the new cultivar are more abundant than flowers and buds of this comparator.
3. Blooming period of the new cultivar is longer than the blooming period of this comparator.
4. Foliage flush color of the new cultivar is bronze, while the foliage flush color of this comparator is burgundy-red.

BRIEF DESCRIPTION OF THE PHOTOGRAPHS

The accompanying photograph in FIG. 1 illustrates in full color a plant of 'FARROWCJWD' grown in a polyhouse in Grand Haven, Michigan.

Figure 1:
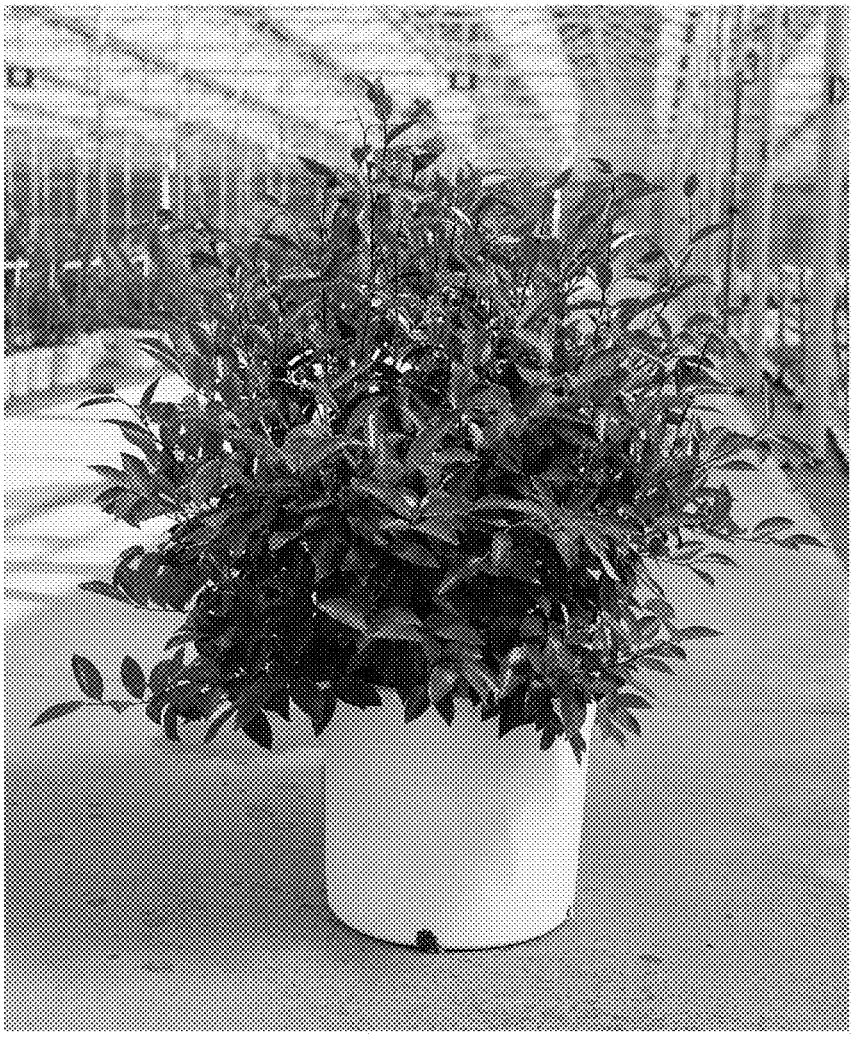
Figure 2:
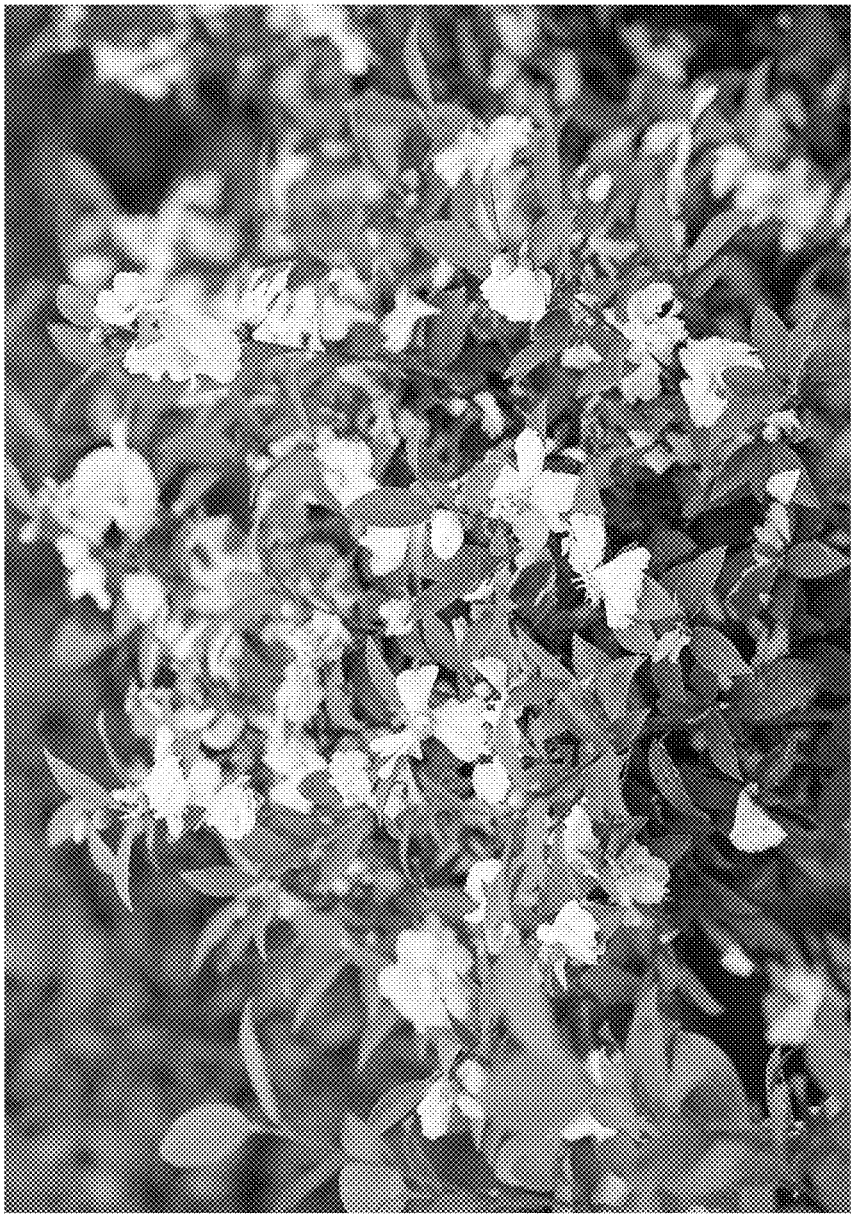
FIG. 2 illustrates a plant grown outdoors in Grand Haven, Michigan.
Figure 3:
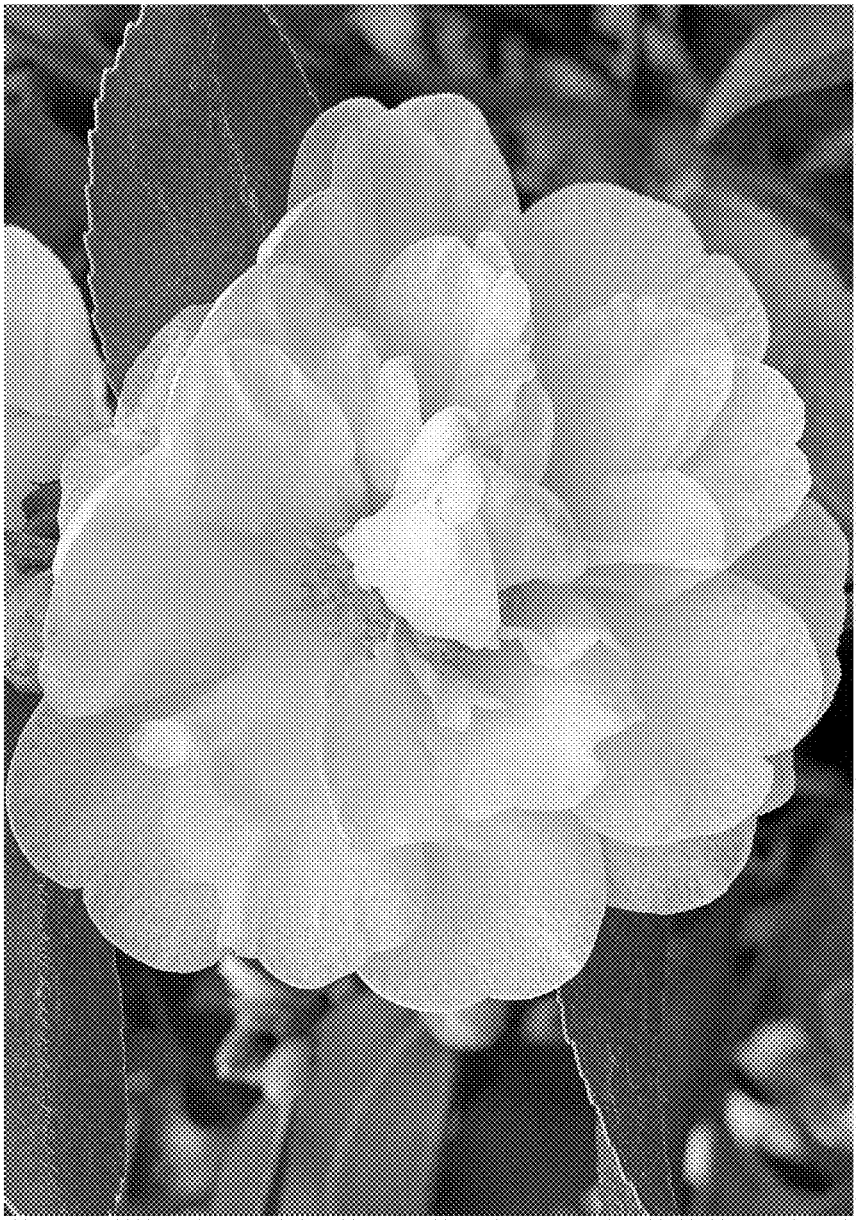
FIG. 3 illustrates a close-up of a flower of 'FARROWCJWD'.

Plants photographed are approximately 4 years old. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'FARROWCJWD' plants grown in a poly-greenhouse in Grand Haven, Michigan in the fall of 2022. Plants are approximately 4 years old, in 3-gallon containers. The average day time temperature is 18-27° C., average night temperature is 5-10° C. Measurements and numerical values represent averages of typical plant types.

Botanical classification: *Camellia* hybrid 'FARROWCJWD'.

PROPAGATION

Method: Hardwood cuttings.

Time to rooting: 4 weeks in summer at 18-27° C.

Root description: Moderately dense, freely branching, thin to medium thickness, and fibrous. Light brown to tannish-white in color, not accurately measured by The R.H.S. Color Chart.

PLANT

Plant type: Evergreen flowering shrub.

Plant shape: Upright.

Growth habit: Upwards.

Height: 115 cm.

Plant spread: 60 cm.

Growth rate: Moderate.

Plant vigor: Good.

Branching characteristics:

*Lateral branches*.—Branching Habit: Basal; some pinching required. Quantity: 10 to 15. Length: 70 cm. Diameter: 3 mm.

*Stem*.—Shape: Rounded. Aspect: 70° to 90°. Strength: Strong, quite rigid. Pubescence: Some, on new growth only. Color: New Growth: RHS Brown 200A to Greyed-Purple 187A. Old Growth: RHS Grey-Brown 199A to 199B.

*Internode length*.—3 cm.

FOLIAGE

Leaf:

*Type*.—Single.

*Arrangement*.—Alternate.

*Length*.—6.5 cm.

*Width*.—4 cm.

*Shape*.—Elliptic.

*Apex*.—Acuminate.

*Base*.—Obtuse.

*Margin*.—Serrulate.

*Texture of top surface*.—Smooth and glossy.

*Texture of bottom surface*.—Smooth and glossy.

*Color*.—Young foliage upper side: Near RHS Brown 200A with tinges of Greyed-Purple 183A. Young foliage under side: Near RHS Brown 200A with tinges of Greyed-Purple 183A. Mature foliage upper side: Near RHS Yellow-Green 147A. Mature foliage under side: RHS Yellow-Green 147B.

*Venation*.—Type: Pinnate. Venation color upper side: RHS Yellow-Green 147B. Venation color under side: RHS Yellow-Green 147B.

Petiole:

*Length*.—5 mm.

*Diameter*.—2 mm.

*Texture, upper side*.—Somewhat pubescent, soft.

*Texture, under side*.—Somewhat pubescent, soft.

*Color*.—RHS Yellow-Green 147B.

FLOWER

Bloom period: Fall.

Flowers:

*Arrangement*.—Single or paired flowers at leaf nodes along length of lateral branches.

*Shape*.—Double whorl.

*Aspect*.—Outwards from lateral stem.

*Quantity of flowers per lateral stem*.—3 to 5.

*Quantity of buds per lateral stem*.—3 to 5.

*Quantity of flowers and buds per plant*.—About 100.

*Length*.—7 cm.

*Diameter*.—7.5 cm.

*Depth*.—4.5 cm.

*Persistence*.—Self-cleaning.

*Fragrance*.—Mildly sweet, spice-like.

Petals:

*Length*.—3.5 cm.

*Width*.—2.75 cm.

*Apex*.—Retuse.

*Base*.—Cuneate.

*Shape*.—Elliptic to obovate.

*Margin*.—Entire.

*Arrangement*.—Double whorl.

*Number*.—About 12.

*Fused*.—No.

*Appearance*.—Smooth.

*Texture*.—Smooth, soft.

*Color*.—Upper surface at first opening: RHS White NN155B. Under surface at first opening: RHS White NN155B. Upper surface at maturity: RHS White NN155B. Under surface at maturity: RHS White NN155B.

Petaloids:

*Length*.—3 cm.

*Width*.—1.5 cm.

*Apex*.—Retuse.
*Base*.—Cuneate.
*Shape*.—Narrowly elliptic, oblong.
*Margin*.—Entire, though some have small (5mm) lobes which may protrude.
*Arrangement*.—Whorl; protrude from center of flower amidst anthers.
*Number*.—15 to 20.
*Fused*.—No.
*Appearance*.—Somewhat irregularly shaped or folded.
*Texture*.—Smooth, soft.
*Color*.—Upper surface at first opening: RHS White NN155B. Under surface at first opening RHS White NN155B. Upper surface at maturity: RHS White NN155B. Under surface at maturity: RHS White NN155B.

Bud:
*Shape*.—Ovoid.
*Length*.—1 cm.
*Diameter*.—0.75 cm.
*Color*.—RHS Yellow-Green 146C to 146D.

Sepals: No noticeable sepals present; sepals are shed upon/shortly after bud break.

Peduncle:
*Length*.—2 mm.
*Diameter*.—2 mm.
*Color*.—RHS Yellow-Green 143C.
*Texture*.—Glabrous.
*Aspect*.—45° relative to stem.
*Strength*.—Strong.

REPRODUCTIVE ORGANS

Stamens:
*Number*.—About 90.
*Filament length*.—1 cm.
*Filament color*.—RHS Yellow 8C.
*Anthers*.—Length: 2 mm. Color: RHS Yellow 8C. Pollen: Quantity: Sparse to none. Color: RHS Yellow 8C. Shape: Club-like.

Pistil:
*Number*.—1.
*Length*.—1 cm.
*Style*.—Length: 0.75 cm. Color: RHS Yellow-Green 145D.
*Stigma*.—Shape: Linear, pistil split into 3. Color: RHS Yellow-Green 145D.

OTHER CHARACTERISTICS

Disease and pest resistance: Neither resistance nor susceptibility to normal pests of *Camellia* observed.
Temperature tolerance: USDA Zones 7(6b)-9.
Fruit/seed: Not observed.

What is claimed is:

1. A new and distinct cultivar of *Camellia* plant named 'FARROWCJWD' as herein illustrated and described.

* * * * *